US009751084B2

(12) United States Patent
Greenizen et al.

(10) Patent No.: US 9,751,084 B2
(45) Date of Patent: Sep. 5, 2017

(54) BIOLOGICAL CULTURE ASSEMBLY

(75) Inventors: Kurt E. Greenizen, Bradford, MA (US); Phillip Clark, Wakefield, MA (US); John J. Doyle, Kensington, NH (US)

(73) Assignee: EMD Millipore Corporation, Billerica, MA (US)

( * ) Notice: Subject to any disclaimer, the term of this patent is extended or adjusted under 35 U.S.C. 154(b) by 723 days.

(21) Appl. No.: 12/589,369

(22) Filed: Oct. 22, 2009

(65) Prior Publication Data

US 2010/0151511 A1 Jun. 17, 2010

Related U.S. Application Data

(60) Provisional application No. 61/197,520, filed on Oct. 28, 2008.

(51) Int. Cl.
*G01N 1/30* (2006.01)
*C12N 5/02* (2006.01)
*B01L 3/00* (2006.01)

(52) U.S. Cl.
CPC ......... *B01L 3/5085* (2013.01); *B01L 3/50853* (2013.01); *B01L 2200/028* (2013.01); *B01L 2200/0689* (2013.01); *B01L 2300/0822* (2013.01); *B01L 2300/0829* (2013.01)

(58) Field of Classification Search
CPC ............... B01L 3/5085; B01L 3/50853; B01L 2300/0829; B01L 2300/0822; B01L 2200/0689; B01L 2200/028; C12M 23/12; C12M 23/04
USPC ..................................... 435/40.5, 395, 305.2
See application file for complete search history.

(56) References Cited

U.S. PATENT DOCUMENTS 3,726,764 A 4/1973 White et al.
3,726,767 A 4/1973 White et al.
3,745,091 A * 7/1973 McCormick .......... B01L 3/5085 156/305
3,883,398 A 5/1975 Ono
5,021,351 A * 6/1991 Ervin ......................... 435/305.1
(Continued)

FOREIGN PATENT DOCUMENTS

EP 0481820 4/1992
EP 0681024 11/1995

OTHER PUBLICATIONS

International Preliminary Report on Patentability received for PCT Application No. PCT/US2009/05743, issued on May 3, 2011, 8 pages.

(Continued)

*Primary Examiner* — William H Beisner
*Assistant Examiner* — Danielle Henkel
(74) *Attorney, Agent, or Firm* — Nields, Lemack & Frame, LLC

(57) ABSTRACT

The invention relates to a single use cell culture assembly for use in carrying out bioreactions and growing microorganisms, and tissue and cell cultures. The cell culture assembly is designed to receive an insert having a microscope slide upper surface, and includes a well frame having a plurality of partitioned well compartments, adapted to be positioned on the upper surface of the insert, and includes a liquid-impermeable releasable seal positioned on or within the lower edge of the well frame for maintaining a liquid-impermeable barrier between well compartments.

14 Claims, 7 Drawing Sheets

(56) References Cited

U.S. PATENT DOCUMENTS

| | | | | |
|---|---|---|---|---|
| 5,417,576 | A * | 5/1995 | Hill | 435/288.3 |
| 5,571,721 | A * | 11/1996 | Turner | B01L 3/5085 359/398 |
| 6,074,874 | A * | 6/2000 | Latimer | 435/404 |
| 6,379,626 | B1 * | 4/2002 | Munson et al. | 422/569 |
| 6,682,703 | B2 * | 1/2004 | Burow et al. | 506/40 |
| 7,731,909 | B1 * | 6/2010 | Grudzien et al. | 422/547 |
| 2004/0071605 | A1 * | 4/2004 | Coonan | B01L 3/50855 422/400 |
| 2005/0048642 | A1 | 3/2005 | Bunn et al. | |
| 2005/0135974 | A1 * | 6/2005 | Harvey | B01L 3/50855 422/400 |
| 2009/0253582 | A1 * | 10/2009 | Pena | B01L 3/5085 506/7 |

OTHER PUBLICATIONS

International Search Report received for PCT Application No. PCT/US2009/005743, mailed on Feb. 2, 2010, 4 pages.

* cited by examiner

BIOLOGICAL CULTURE ASSEMBLY

CROSS-REFERENCED TO RELATED APPLICATIONS

This application claims the benefit of U.S. Provisional Patent Application No. 61/197,520, filed on Oct. 28, 2008 the entire contents of which are incorporated by reference herein.

DESCRIPTION OF THE INVENTION

Field of the Invention

The present invention relates generally to biological culture assemblies or vessels. More particularly, it relates to a resealable or a single use cell culture assembly for receiving microscope slide inserts, as well as kits and methods relating to using the assembly.

Background of the Invention

Cell culture vessels such as slides, flasks, dishes, tubes and the like are commonly used in biological research, medical laboratory practices, and biomedical diagnostic applications to grow and culture various cell and tissue test samples, as well as testing for the presence of microorganisms in mammalian cell and tissue test samples.

One method used to detect the presence of a microorganism causing an infection is to attempt to isolate and culture the microorganism from a patient in an artificial medium that permits the growth of selective microorganisms. If the microorganism is present in the patient's specimen, it will grow in the medium whereby both the presence and number of microorganisms in a patient's specimen can be determined to assist in defining the cause of a disease.

In order to grow or culture cells on a solid surface of a cell culture vessel, liquid growth medium is typically needed. The solid surface provides a location upon which the cells can adhere, and the liquid growth medium typically mimics the cell's natural environment in the tissue from which they were derived, and can include water, salts and amino acids, to which supplements such as serum, antibiotics, growth factors and the like can be added. Often, flat surfaces of tissue-culture flasks, trays, Petri dishes, multi-well culture plates, and other cell culture vessels make ideal support surfaces for growing cells.

Cell culture slides and other types of cell culture vessels typically include single or multiple discrete chambers or wells in which test cell and tissue cultures may be grown. These chambers or wells permit the formation of a reservoir for holding a mixture of cells or tissue and a culture medium, while the flat upper surface of the slide and the like form a solid support surface to which the cultured cells or tissue adhere. As the cell or tissue culturing process advances, progress may be monitored by viewing the cells from the bottom of the slide, such as with the aid of an inverted microscope and the like. Once the cell culture has reached the desired state of growth, the culture media is removed and the chamber is removed from the slide, leaving the cells attached to the flat surface of the slide in an undisturbed state and ready for subsequent testing.

An example of a cell or tissue culture vessel for carrying out biological reactions or growing tissue or cell cultures is taught in U.S. Pat. No. 3,726,764 issued to White, which teaches a cell culture vessel having a growth chamber adhered to a glass slide via a liquid-impermeable silicone based adhesive seal. The silicone present in the adhesive can leach onto the upper surface of the glass slide, creating a surface that may not be conducive to cell growth. A special tool is wedged into the adhesive seal to separate the chamber from the glass slide. However, common problems or conveniences which often confront users of this type of cell culture vessel include: 1.) using a separate tool to remove the chamber from the slide is not convenient, 2.) the potential for shattering the glass slide when attempting to separate the chamber from the slide is always present, 3.) the contamination of the cells on the slide is always a possibility, 4.) the adhesive seal typically remains at least partially adhered to the slide when the chamber is removed, such that as the seal is pulled off, an aerosolizing effect can occur, creating a potential biohazard by sending cell or tissue culture material into the air, 5.) the potential for disturbing the cell and tissue cultures adhering to the upper surface of the slide, and 6.) the cumbersome nature of the process for removing the chamber and adhesive seal takes additional lab time.

Another example of a conventional cell culture vessel is a multi-well slide assembly, such as the Nunc™ SonicSeal Slide™ four well slide available from Nalgene Nunc International, (Rochester, N.Y. U.S.A.) a Thermo Fisher Scientific Company. The SonicSeal Slide™ includes multiple wells joined together and secured to a slide plate through a breakable ultrasonic weld. As also taught in White discussed supra, a tool or opener is required to remove the upper structure of the wells from the slide plate in order to analyze the cell culture disposed on the slide plate.

Multi-well cell culture plates may also be used for bioreactions and diagnostic testing applications in addition to growing cell cultures. Multi-well plates have multiple wells formed into a two-dimensional array within which one or more cell lines are grown. Often, however, such multi-well plates are restrictive in that it is difficult to grow multiple and/or different cell lines on a single plate due to differing culture times and media requirements for each type of cell line. Moreover, there is a possibility of cross-contamination between wells on the same slide. In addition, if one cell culture in a multi-well plate becomes contaminated or otherwise inoperative, typically the entire plate along with all of the cell lines growing thereon must be discarded.

Many conventional biological culture vessels are typically not well suited for successfully performing a variety of operational, analytical, and logistical tasks required in tissue and cell culturing. For example, biological culture vessels such as vials, culture tubes and petri dishes are often suitable for inoculation and/or incubation however, such vessels are typically not well suited for tissue and cell culture analysis. Consequently, test biological samples often must be transported and/or stored between different vessels during the culturing process. Moreover, when using vials, culture tubes and petri dishes, each test cell and tissue sample must be handled individually, which is cumbersome, time consuming, and inefficient when working with numerous test biological samples.

Therefore, it is desirable to have a cell culturing vessel, such as a microscope slide and the like, onto which a well frame having one or more well compartments can be releasably attached. It is also desirable to have well compartments that are liquid-impermeable when sealed to the upper surface the cell culturing vessel without having an adhesive and/or sealant material leach onto the upper surface of the vessel, thereby contaminating the cell cultures grown thereon, or leaves behind an adhesive and/or sealant material on the upper surface of the vessel. An adhesive or sealant material left behind on the upper surface of the vessel can be difficult to remove, and potentially creates an unnecessary biohazard to a user attempting to remove the adhesive material.

Therefore, a need exists for an improved biological culturing assembly and enhanced methods of performing culturing, differentiating, testing, storing and transporting of biological test samples with greater, efficiency, reliability, accuracy and safety. Particularly an improved cell culturing assembly and enhanced methods of using the same that are well suited for facilitating a variety of biological, chemical and medical research activities of cell and tissue test samples, with minimal manipulation of the assembly components, while minimizing the time, effort, and potential contamination concerns associated with transferring and transporting different types of tissue and cell cultures between different culturing vessels.

Accordingly, it would be desirable to have an improved cell culturing assembly, kit and methods of using the same directed to addressing these and other issues and challenges confronting researchers and scientists growing, differentiating, testing, storing and transporting biological test samples.

SUMMARY OF THE INVENTION

It is therefore a primary object of this invention to address these and other needs and problems associated with current tissue and cell culture vessels, by providing a new, single use or resealable biological culture assembly having various components that alone or in combination facilitate biological, chemical and molecular bioreactions, analysis, testing, and culturing cell and tissue test samples with minimal manipulation of the assembly components. Thus, in accordance with the teachings of the present invention a new and easy to use cell culture assembly is provided capable of providing a user the ability to conduct various biological, chemical and molecular operations and analysis of different or similar test cell samples on the same cell culture assembly insert, thereby speeding up biological sample testing and culturing, while minimizing cross-contamination between multiple test samples, which in turn provides for savings in cost and time. Other advantages of the various embodiments of the invention will be apparent to one skilled in the art.

The invention relates to a resealable (i.e., reusable) or single use biological culture assembly for receiving a base member insert for use in carrying out biological, molecular and chemical bioreactions and growth therein, such as growing cultures of microorganisms, tissue and cell test samples, as well as storing and transporting the same. The cell culture assembly receives a base member insert having an upper surface, such as standard or customized microscope slides, and includes a support frame for receiving the slide, and a sealable well compartment frame having one or more well compartments, upper and lower well compartment openings, sidewalls, upper and lower surfaces, and upper and lower edges. The sealable well frame is adapted to be operatively positioned on the upper surface of the base member insert, and includes a liquid-impermeable sealing means positioned on or within the lower surface of the well frame. The sealing means is adapted to, operatively create a liquid-impermeable releasable seal or barrier when the lower surface of the well frame is positioned over the upper surface of the base member insert and the sealing means is compressed or otherwise sealingly engaged to the upper surface of the base member insert. The assembly may also include a cover positioned over the upper well compartment opening. When the assembly is in a closed position, the well frame can be secured to the support frame by a variety of fastening or attachment means.

In certain embodiments, the present invention provides a cell culture assembly wherein the sealing means is an integral over-molded thermoplastic elastomer (TPE), or synthetic or natural rubber material positioned on the lower surface of the well compartment frame. Alternatively, the sealing means is a TPE or synthetic or natural rubber material located within a groove or channel on the lower surface of the well frame, or the sealing means is a TPE or synthetic or natural rubber material adhesively bonded onto the lower surface of the well frame. The TPE or synthetic or natural rubber material located within a groove on the lower surface of the well frame may additionally be adhesively bonded to well frame.

In another embodiment, the present invention provides a one-piece cell culture assembly wherein the well frame is attached to the support frame by an attachment means such as a hinge or the like. The well frame is preferably hinged at about 180 degrees to the support frame such that when the assembly is in a closed position the liquid-impermeable sealing means positioned on the lower surface of the well frame becomes compressed against or otherwise sealingly engaged to the upper surface of the slide insert, thereby isolating each of the well compartments within the well frame from each other. Additionally, a fastening means such as one or more hinged snap tabs mounted on the support frame engage one or more snap tab catches mounted on the well frame. Preferably, the snap tab is hingedly attached to the support frame at about 90 degrees, such that the when the assembly is in a closed position, the snap tab engages the snap tab catch thereby holding the assembly closed.

In yet other embodiments, the invention provides a biological culture assembly having a stacking means, such as a plurality of stacking ribs or the like incorporated into the top surface of the cover, thereby allowing multiple assemblies to be arranged in a stacked configuration, one on top of the other, to conserve space in a hood and in an incubator.

In still other embodiments, the present invention provides a biological culture assembly having condensate management features such as elongated ridges located on the underside of the cover. These ridges act to isolate individual well compartments, thereby containing condensation within the perimeter of each individual well compartment.

In still other embodiments, the present invention provides a biological culture assembly having improved methods for carrying out biological reactions on multiple and/or different test biological samples on the upper surface of the same slide insert by preventing contamination between each individual biological sample well compartment. When the well frame is positioned on the upper surface of the slide insert, the sealing means is compressed against or otherwise sealingly engaged to the upper surface of the slide insert, thereby maintaining the integrity of each individual biological reaction due to the presence of the liquid-impermeable sealing means forming a barrier and separating each well compartment from each other In another embodiment, the present invention provides a biological culture assembly having substantially reduced detachment forces between the resealable well frame and the upper surface of the slide insert when the well frame and slide insert are joined by the liquid-impermeable sealing means, in comparison to conventional cell culture vessels, such that the well frame is easily separated and removed from the upper surface of the slide insert, without the need of a separate tool, such as a lever, wedged into the seal formed between the well frame and the slide insert as conventionally done.

Consistent with a further aspect of the invention, a cell culture assembly system is provided including a slide insert, a support frame for receiving the slide insert, and a multi-well compartment frame having a liquid-impermeable seal on its lower surface. A liquid-impermeable barrier or seal surrounds each of the plurality of well compartments that are formed on the upper surface of the slide insert when the multi-well frame is positioned on the upper surface of the slide insert, and the liquid-impermeable seal is compressed onto or otherwise sealingly engaged with the upper surface of the slide insert. In preferred embodiments, the liquid-impermeable seal comprises an over-molded or adhesively bonded gasket, O-ring or other sealing structures, made from TPE (thermoplastic elastomer), or synthetic or natural rubber. The seal may also be located within a groove or channel on the lower surface of the well frame, In another embodiment, the present invention provides a slide insert constructed of plastic and having open through holes that are in positional alignment with the well compartments of the well frame in the cell culture assembly, wherein at least one of the open through holes is covered by a porous matrix or membrane, such as a hydrophilized polytetrafluoroethylene (PTFE) membrane.

In yet other embodiments, the invention provides a kit for tissue and cell culturing comprising one or more microscope slides, one or more cell culture assemblies having a support frame for receiving slides inserts, and a resealable well compartment frame having a liquid-impermeable sealing component positioned on the bottom surface of the well frame and adapted to be operatively positioned and compressed onto the upper surface of the microscope slide such that the sealing component seals the lower surface of the well frame to the upper surface of the microscope slides. The assembly may also include a removable cover positioned on the upper surface of the well frame, covering the well compartment openings. Additionally, the kit may include plastic or glass microscope slides having open through holes that can be positionally aligned with the well compartments of the well frame, such that at least one of the open through holes is covered with a porous membrane, such as a hydrophilized Polytetrafluoroethylene (PTFE) membrane. The kit may also comprise cells, reagents, media, growth factors, and protocols.

In still other embodiments, the present invention provides methods, techniques and procedures for growing cell and tissue test sample cultures in a cell culture assembly comprising: a.) positioning the slide insert, such as a standard or customized microscope slide insert, onto the support frame; b.) operatively positioning and compressing the well compartment frame having the sealing means located on or within its lower surface onto the upper surface of the slide insert such that the sealing means creates a liquid-impermeable seal or barrier between the lower surface of the well frame and the upper surface of the slide insert, thereby forming one or more well compartments on the upper surface of the base member insert; c) placing a cell culture medium into each individual well compartment onto the upper surface of the slide insert; d.) introducing a biological test sample, such as a liquid tissue or cell sample, into the cell culture medium positioned on the slide insert; e.) incubating the medium and tissue or cell test sample under appropriate conditions to allow the sample to grow and to attach itself to the upper surface of the slide insert; f.) removing the cell culture medium from each well compartment; g.) washing, fixing, and/or staining cell or tissue cultures directly in well compartments; h.) separating the well compartment frame and the slide insert having the cell or tissue cultures attached onto the upper surface of the slide insert, followed by; i.) microscopically examining the attached cell or tissue cultures as desired. Alternatively, step h.) can occur prior to step g.), whereby the washing, fixing, and/or staining of cell or tissue cultures occurs after the well compartment frame has been separated from the upper surface of the slide insert.

These and other advantages and features, which characterize the invention, are set forth in the claims annexed hereto and forming a further part hereof. However, for a better understanding of the invention, and of the advantages and objectives attained through its use, reference should be made to the drawings, and to the accompanying descriptive matter, in which there is described exemplary and explanatory embodiments of the invention, which are intended to provide an explanation of various embodiments of the present teachings. The specific embodiments described herein are offered by way of example only and are not meant to be limiting in any way.

DESCRIPTION OF THE EMBODIMENTS

One skilled in the art will appreciate that the expression "cell culture" when used throughout the specification also includes "tissue culture", because tissues are a higher organization of cells. In addition, the expression "biological culture" when used throughout the specification includes, but is not limited to, cell, tissue, and microorganism cultures For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about".

As used herein, the singular forms "a", "an", and "the" include plural referents unless the context clearly dictates otherwise.

The present invention provides and teaches, in various embodiments, cell culture assemblies and methods for performing and facilitating biological, chemical and molecular reactions, testing, growing, differentiating, transporting and storing biological culture samples within the assemblies, while minimizing cross-contamination between multiple test samples on the same slide insert.

The Assembly

Figure 1:
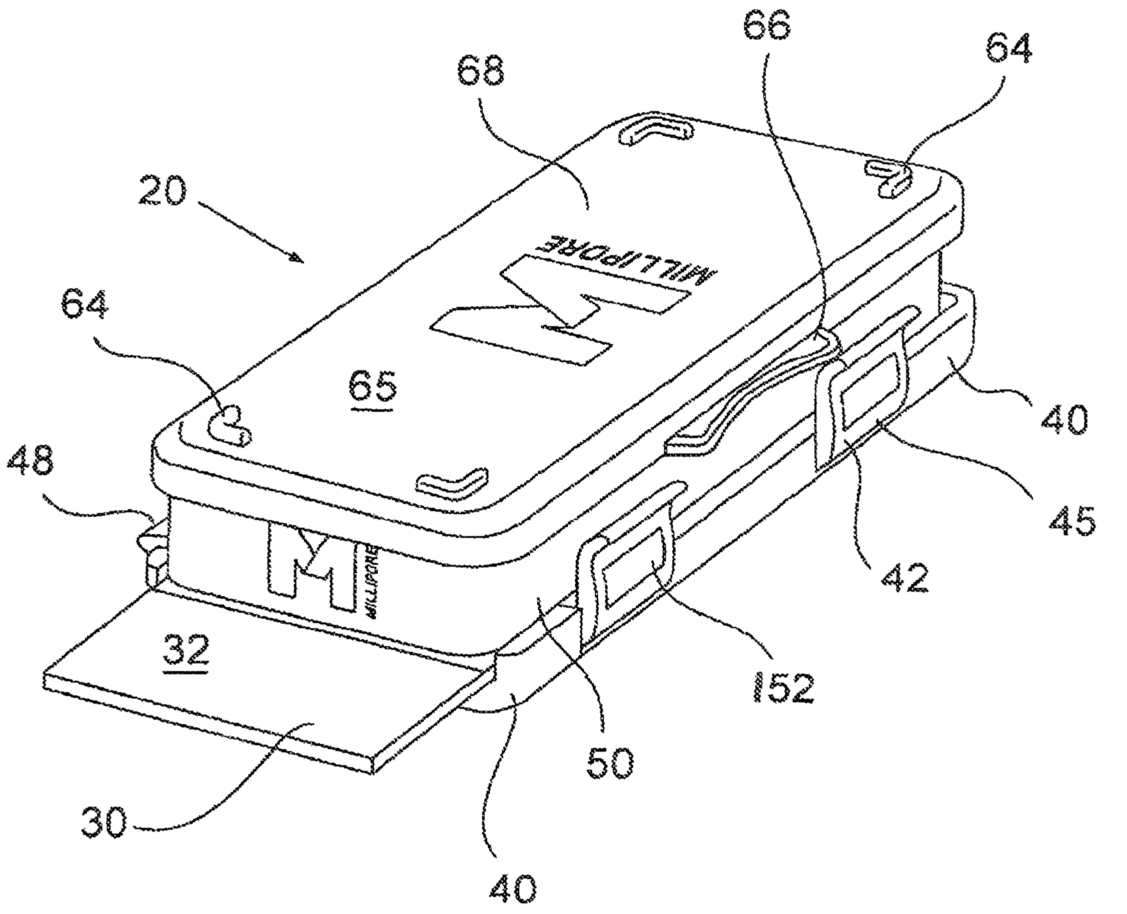
FIG. 1 is a perspective view of an assembled cell culture assembly in the closed position, in accordance with aspects of the present invention.
Figure 2:
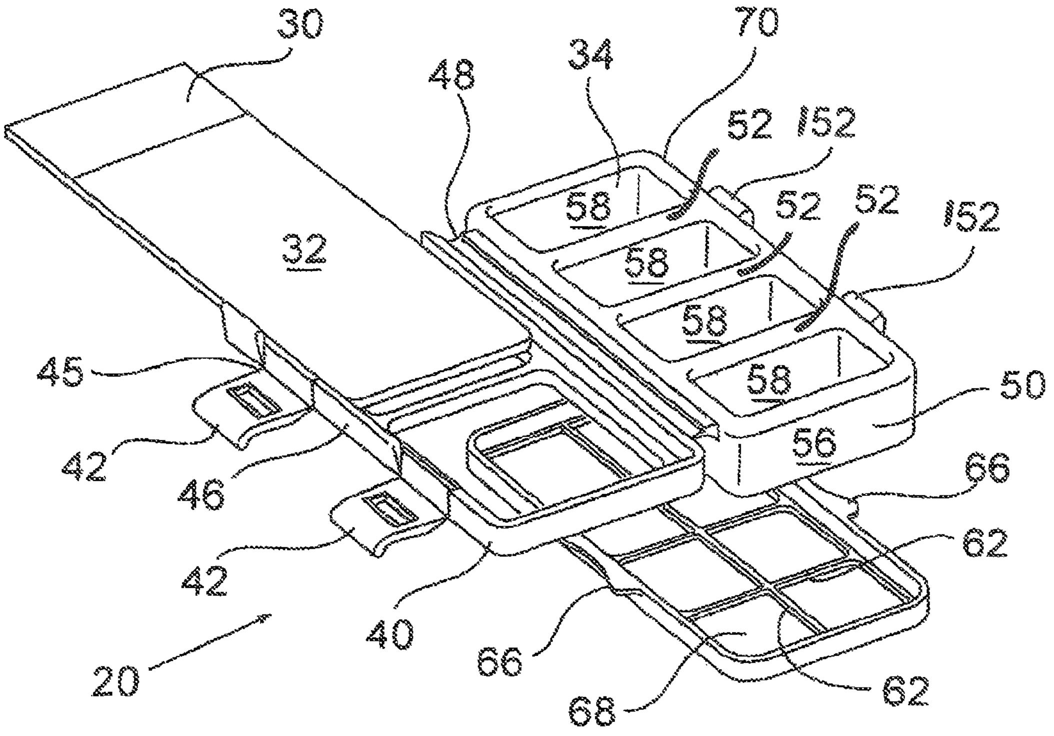
FIG. 2 is a perspective view of a partially assembled cell culture assembly in the opened position, in accordance with aspects of the present invention.
Figure 3:
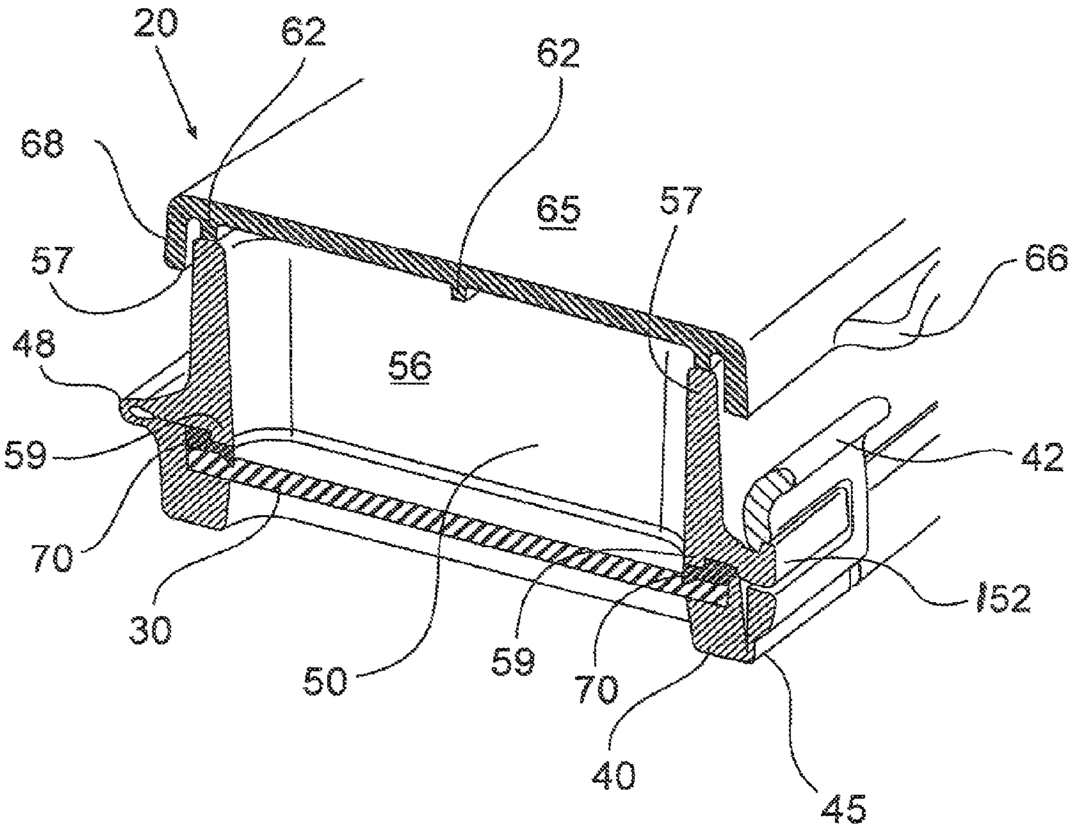
FIG. 3 is a perspective side view of the assembled cell culture assembly in FIG. 1 with part of the assembly cut away; in accordance with aspects of the present invention.
Figure 4:
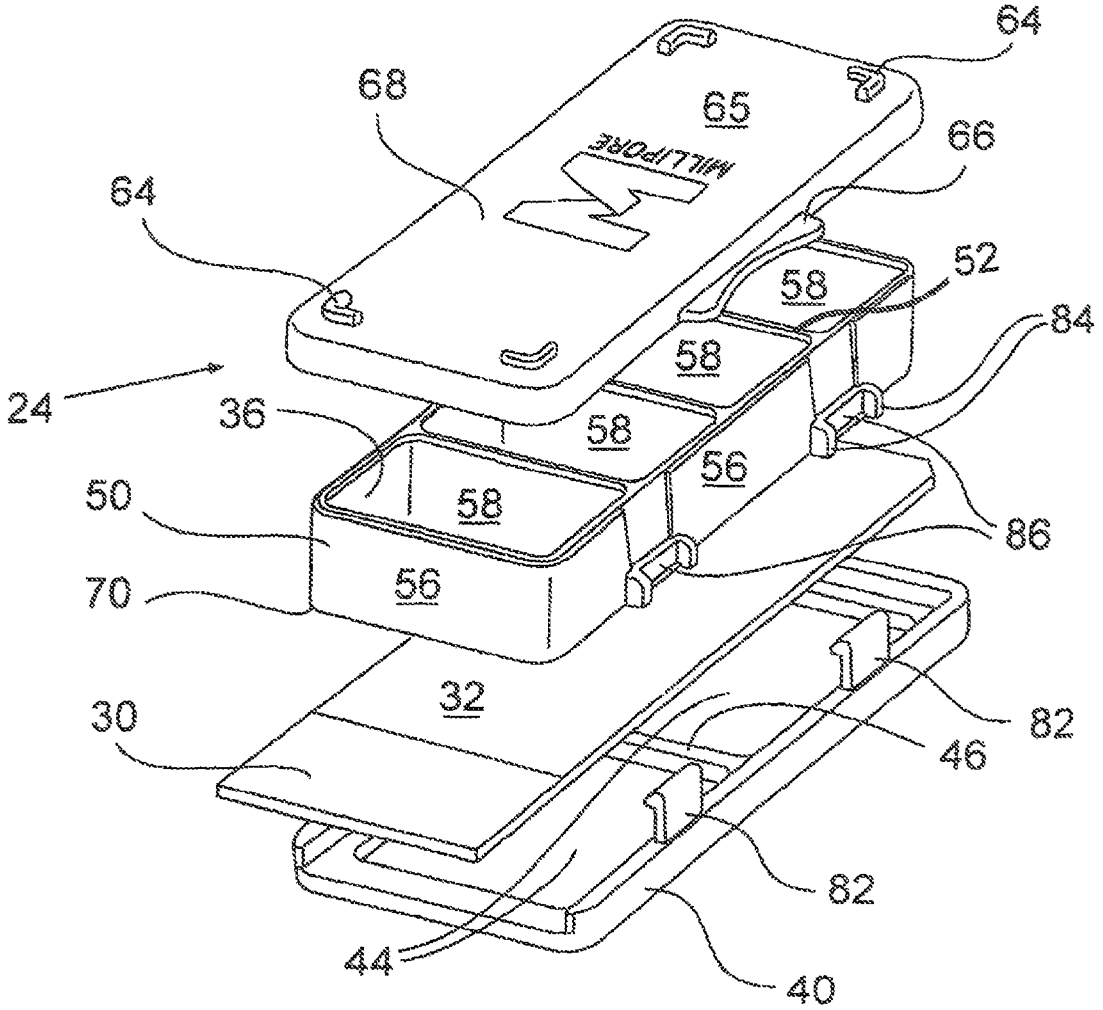
FIG. 4 is a perspective view of a disassembled cell culture assembly, in accordance with aspects of the present invention.
Figure 5:
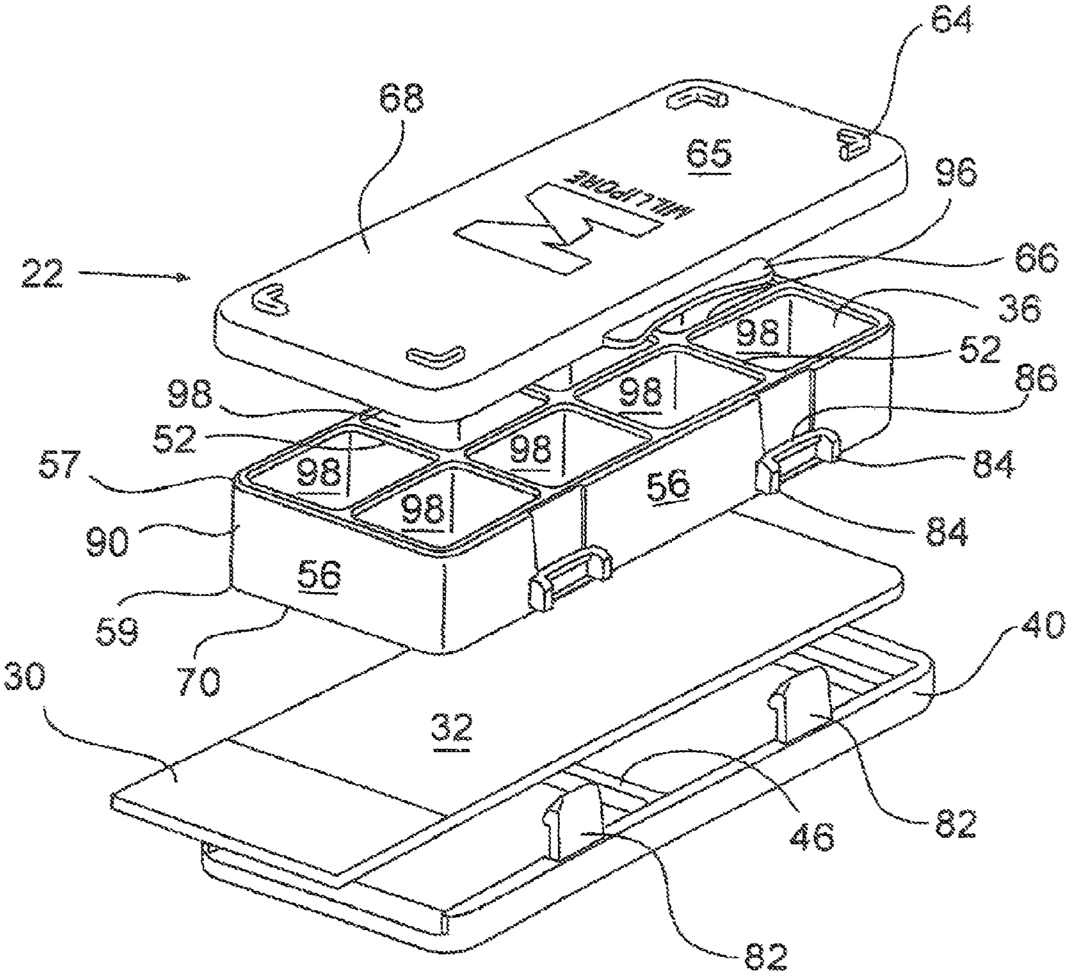
FIG. 5 is a perspective view of a disassembled cell culture assembly, in accordance with aspects of the present invention.

As shown in FIGS. 1-3, and in accordance with one aspect of the invention taught herein, a cell culture assembly 20 comprises a one-piece assembly consisting of a support frame 40 for receiving a base member insert 30 attached to a releasable sealable well compartment frame 50. As shown in FIGS. 4 and 5, and in accordance with another aspect of the invention taught herein, cell culture assembly 22, 24 comprises a two-piece assembly having a support frame 40 for receiving a base member insert 30 and a releasable sealable well compartment frame 50, 90, wherein support frame 40 and well compartment frame 50, 90 are not attached as in the one-piece assembly 20, but are two separate and distinct unattached components.

As shown in FIG. 2, the well compartment frame 50 is adapted to be operatively positioned onto the upper surface 32 of the base member insert 30. Well compartment frame 50 includes upstanding sidewalls 56 having upper 57 and lower 59 surfaces with upper and lower edges, and one or more well compartments 58, wherein each well component has an upper 36 and lower well 34 compartment openings. A sealing means 70 is positioned on or in the lower surface 59 of the well frame 50.

In accordance with another aspect of the invention taught herein the base member insert 30 comprises standard and customized glass or plastic microscope slides and the like. Sealing means 70, as shown in FIGS. 2-6, is located on or in the lower surface 59 of the well frame sidewalls 56 and the well compartment sidewall partitions 52, 96, is adapted to releasably seal at its point of contact with the upper surface of the base member insert 30, thereby forming a liquid-impermeable seal or barrier.

As shown in FIGS. 2, 4, 5 and 6, well compartment frame 50 can include one or more transverse extending well compartment sidewall partitions 52, which are preferably parallel to and preferably spaced equidistant from a pair of opposing sidewalls 56. FIG. 2 depicts three transverse extending well compartment sidewall partitions 52. Depending upon the number of well chambers desired for the assembly, the well compartment frame 90 may include, as depicted in FIG. 5, one or more longitudinally extending well compartment sidewall partitions 96, which are preferably longitudinal to and preferably spaced equidistant to a pair of opposing sidewalls 56. FIG. 5 depicts one longitudinally extending sidewalls partition 96.

The partitions and sidewalls form a unitary compartmentalized structure that define, as taught in these embodiments, cubicle well compartments in the well frame 50, which are configured to maintain and keep separate each biological and/or chemical test sample within each individual well compartment from contaminating other biological and/or chemical test samples within their own individual well compartments.

While well chambers 58, 98 in the well frames 50, 90 respectively, depicted in FIGS. 1, 2, and 4-6 have four-sides, and generally have rectangularly-shaped cross-sections, one skilled in the art would appreciate can have more or fewer sides, as well as other cross-sectional geometric shapes, including but not limited to for example, spherically shaped cross-section chambers.

While the assemblies taught and depicted herein contain four well compartments 58 as shown in FIGS. 1, 2, 4 and 6, or eight well compartments 98 as shown in FIG. 5, it is understood that the present invention covers assemblies that contains at least one chamber and can contain can contain any desired number of well compartment.

The number of well compartments used in the assemblies taught herein can be configured in any number, including but not limited to 1, 2, 3, 4, 8, 96, 384, etc., wherein the number of well compartments would be dependent upon the application, and other factors required to carry out the specific biological and chemical processes and procedures used to practice the invention.

Furthermore, the assemblies 20, 22, and 24 may include indicia for identifying the different well compartments, or identifying different positions on the upper surface of the slide insert corresponding to a particular cell or tissue culture formed thereon, just to name a few. (not shown)

Sealing Means

Figure 6:
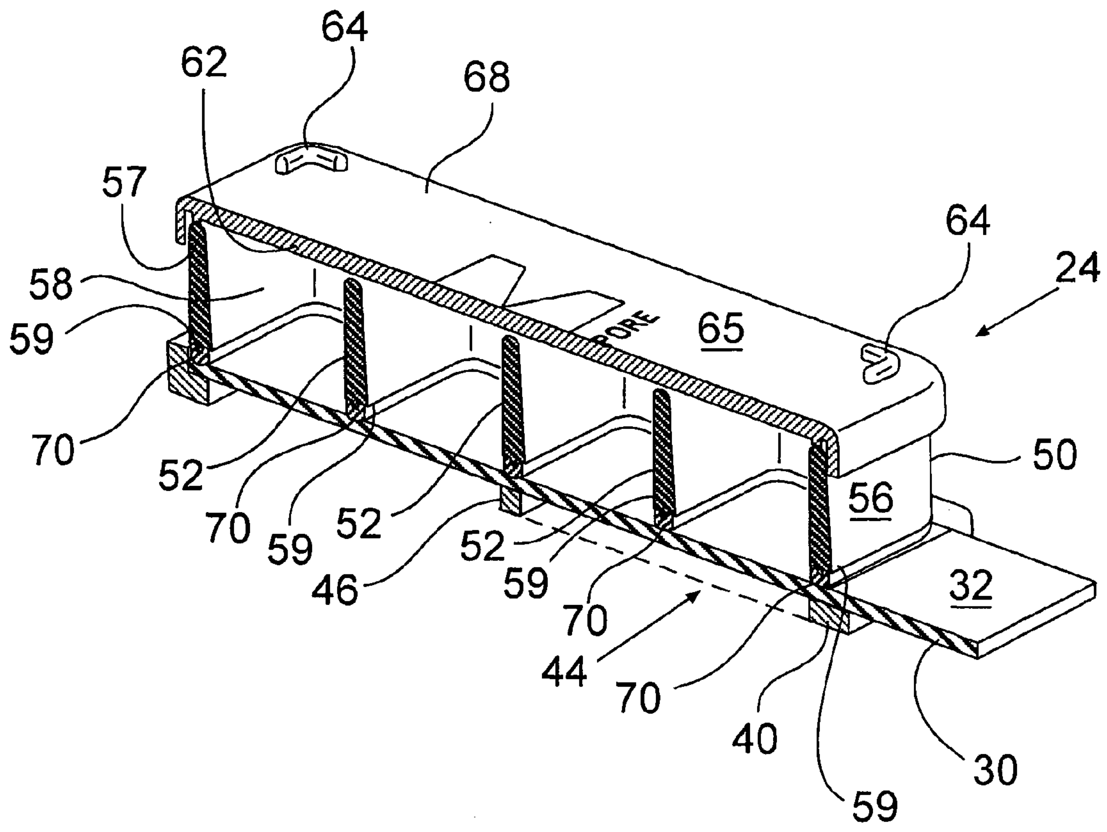
FIG. 6 is a perspective side view of an assembled cell culture assembly similar to the assembly in FIG. 4, with part of the assembly cut away, in accordance with aspects of the present invention.

As shown in FIGS. 2, 3 and 6, and in accordance with one aspect of the invention taught herein, the sealing means 70 is located on or in the lower surface 59 of the well frame sidewalls 56 and the well compartment sidewall partitions 52, 96, and is adapted to operatively create a liquid-impermeable releasable seal or barrier when the well frame 50 is matingly positioned and aligned over the upper surface 32 of slide insert 30, such that the releasable sealing means 70 is compressed on or otherwise sealingly engaged with the upper surface 32 of the slide insert 30.

The liquid-impermeable sealing means 70 can be an integral, over-molded thermoplastic elastomer (TPE) material, synthetic or natural rubber material, or other similar such materials, positioned along or in the lower surface 59 of the entire well frame 50 sidewalls 56, and the well sidewall compartment partitions 52, 96.

Alternatively, the liquid-impermeable sealing means 70 can be a TPE, synthetic or natural rubber material, or other similar such materials, located within a groove or channel (not shown) on the lower surface of the sidewalls 56 and the well sidewall compartment partitions 52, 96, or a TPE, rubber material, or other similar such materials adhesively bonded within a groove or channel on the lower surface of the sidewalls 56 and the well sidewall compartment partitions 52, 96.

The TPE, natural and synthetic rubber material, or other similar such sealing materials can comprise a compressible cut gasket, O-ring or other similar such sealing material adhesively attached to the lower surface of the sidewalls 56 and the well sidewall compartment partitions 52, 96 of the well frame 50.

Liquid-impermeable sealing means 70 can also be retained on the lower surface of the sidewalls 56 and the well sidewall compartment partitions 52, 96 of the well frame 50 by mechanical means such as a tabs or the like (not shown) either in combination with an adhesive or in lieu thereof.

Some of the criteria for a useful liquid-impermeable sealing means material as used herein are that it provides a desired compressible, releasable, and easily removable seal between the lower surface 59 of sidewalls 56 and the well sidewall compartment partitions 52, 96 of well frame 50 and the upper surface 32 of slide insert 30. Additionally, the liquid-impermeable seal or barrier should be non-toxic to biological cell and tissue cultures subsequently employed in the use of the assembly, and do not also act as a source of growth for any unwanted microorganisms.

Because the liquid-impermeable sealing means 70 is adapted to operatively create a liquid-impermeable, easily releasable seal or barrier when compressed against or otherwise sealingly engaged to the upper surface 32 of base member insert 30, the level of force needed to detach the well frame 50 from the slide insert 30 is substantially reduced. Since well frame 50 is easily removed from the upper surface 32 of base member insert 30, a user of the assembly does not have to use a separate tool or lever to wedge into the sealant or adhesive located between the well frame and the base member insert in order to detach the well from the base as is currently done in the field.

Attachment Means

As shown in FIGS. 1 and 3, the one-piece assembly 20 comprises a well frame 50 attached to the support frame 40 by an attachment means such as hinge 48, or the like. Well frame 50 is preferably hinged at about a 180 degree angle to the support frame 40, such that when the assembly 20 is in the closed position as depicted in FIGS. 1, 3 and 7A-B, sealing means 70, positioned on the lower surface 59 of sidewalls 56 and well sidewall compartment partitions 52, 96 of the well frame 50, becomes compressed against or otherwise sealingly engaged with the upper surface 32 of slide insert 30, thereby isolating each individual well compartment 58 from each other.

Alternatively, well frame 50 can be made from a material which would promote sealing to the upper surface of the slide insert 30 without a secondary or separate sealing means 70, either through the use of a malleable and/or compressible well frame material, or a specific sealing geometry to interface with a specific sealing geometry on, the upper surface of the insert, in order to sealingly engage the well frame 50 with the upper surface 32 of the slide insert 30.

Fastening Means

In accordance with other aspects of the invention taught herein, FIGS. 1-3 show, a fastening means such as one or more hinged snap tabs 42 mounted on the support frame 40 for engaging one or more snap tab catches 152 mounted on the well compartment frame 50, wherein the snap tab 42 is hingedly attached to the support frame 40, preferably at about a 90 degree angle, such that when assembly 20 is in the closed position, as depicted in FIGS. 1,3, 7A, and 7B, snap tab 42 engages the snap tab catch 152, thereby holding the assembly 20 in a closed position.

Assembly 20 is closed by pressing the well compartment frame 50, having the sealing means on the lower surface 59 of sidewalls 56 and well sidewall compartment partitions 52, 96 of well frame 50, downward against the slide insert 30, isolating the well compartments, and engaging snap tabs 42 with the snap catches 152, thereby holding assembly 20 in a closed position.

As shown in FIGS. 2 and 6, support frame 40 can also include a cross member support means 46 for supporting the base member insert 30, and to apply additional force to insert 30 while compressing or otherwise sealingly engaging sealing means 70 when the assembly is closed. In addition, the location and the number of support means 46 are designed to provide adequate rigidity to the support frame 40, and to ensure appropriate alignment and engagement of the fastening means.

In order to remove slide insert 30 from the assembly, snap tabs 42 are flexed outwardly to disengage from the corresponding snap catches 152, thereby allowing the assembly 20 to be opened. In a preferred embodiment, the closure of the assembly can be achieved with either four sets of snap tabs 42, such that there are two sets of snap tabs 42 on either side of the assembly, or only two sets of snap tabs 42 and a hinge 48 or the like, wherein the two sets of snap tabs are on the same side of the assembly.

In the two-piece assemblies 22 and 24, shown in FIGS. 4 and 5, the snap tab catch 86 includes snap tab guide ribs 84, to help ensure a proper alignment of well frame 50, 90 and support frame 40, when the two-piece assembly is in the closed position (not shown) and the snap tab catch 86 engages snap tab 82.

Assembly Cover

In accordance with other aspects of the invention taught herein, the assemblies 20, 22, 24 can include a cover or lid 68 removably coupled to and positioned on the upper surface of the well frame sidewalls to at least partially cover the interior of the well frame 50, thereby enclosing the well compartment openings. The lid 68 is adapted to be used with the well frame 50 to minimize contamination and evaporation in each well compartment, while also providing for air/gas exchange to maintain the pH of the culture medium and liquid reagents contained in each well compartment. As shown in FIGS. 2 and 3, cover 68 includes condensate management features such as elongated ridges 62 located on the underside of the cover. Ridges 62 act to isolate individual well compartments 58, 98, thereby containing condensation within the perimeter of each individual well compartment.

As shown in FIGS. 1 to 7B, cover 68 includes a substantially flat top wall and one or more sidewalls projecting downwardly from an edge thereof. Cover 68 is sized and shaped to fit over the upper end of the well frame 50. In one embodiment, the cover 68 fits with a substantially close fit, as is standard in the industry for bioassays and the like. Thus, in one embodiment, cover 68 may be generally square having sidewalls that in combination with a top wall form cover 68. While other shapes and sizes for the cover 68 are possible, the shape of the cover should generally correspond to the shape of the well frame 50 that is to be covered.

As shown in FIGS. 1-5 and 7A-B, cover 68 additionally has one or more tabs or finger grips 66 projecting from the cover to assist in handling the cover.

Figure 7A:
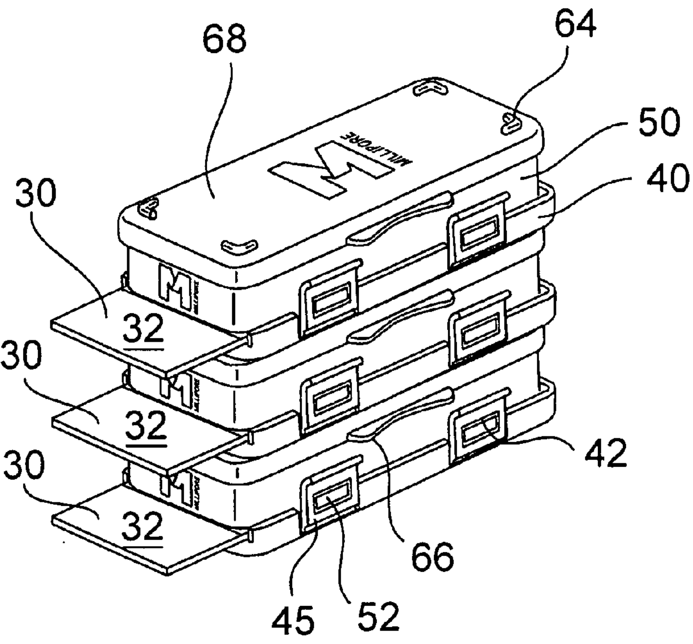
FIG. 7A is a perspective view of cell culture assemblies, similar to the assembly in FIG. 1, in an assembled stacked configuration, in accordance with aspects of the present invention.
Figure 7B:
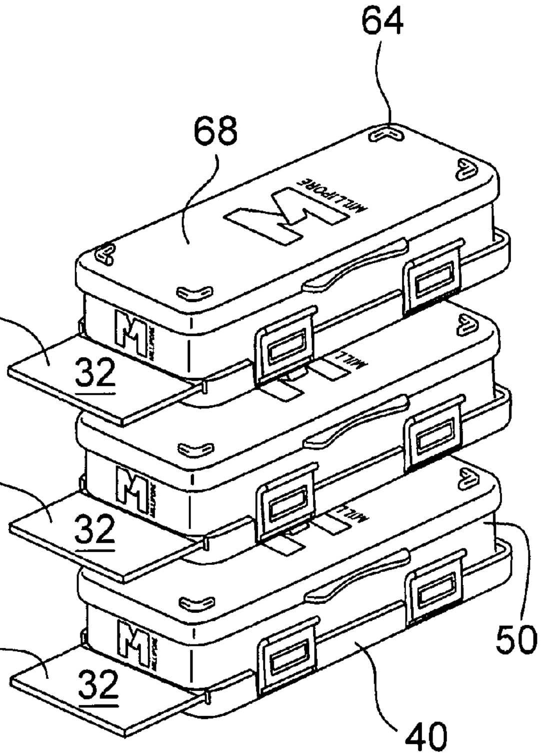
FIG. 7B is a perspective view of cell culture assemblies in FIG. 7A, in a disassembled stacked configuration, in accordance with aspects of the present invention.

Additionally, as shown in FIGS. 1, and 4 to 7A-B, cover 68 may also include raised projections or stacking ribs 64 designed to limit lateral sliding or slippage of one assembly relative to an adjacent assembly when the assemblies are in a stacked configuration, as shown in FIG. 7A. Stacking ribs 64 are located on the upper outer surface 65 of the cover 68, and are positioned to allow assemblies to be stacked together to conserve space under a hood and/or incubator. The stacking of multiple cell culture assemblies could also be accompanied by a rack or "docking station" for enhanced stacking stability during use. (not shown) The cell culture assembly may also include additional features in accordance with alternate embodiments. For example, in one embodiment, two to about ten or more cell culture assemblies may be stacked in a stable manner.

Method of Use

In accordance with other aspects of the invention taught herein, in the assemblies 20, 22, 24 sealing means 70 forms a removable liquid-impermeable seal between each well compartment 58, 98 and the upper surface of base member insert 30 to prevent any leakage from or between the well chambers. The same or different media and cells can be placed in each of the well chambers The desired liquid tissue culture medium (not shown) containing a suspension of cells to be grown in the assembly is placed into each of the well chambers 58, 98 and onto the upper surface 32 of the base member insert 30. The top of the well frame is then covered with cover 68. The assembly is then placed in a suitable incubator and incubated under well-known conditions to carry out the cell and tissue culture growth. If desired, suitable treatment is carried out on the media during the cell growth to achieve desired growth and changes in the cell and tissue cultures. At the conclusion of the growth period, a mass of tissue and cells (not shown) is attached to the upper surface of the base member insert within each of the well compartments of the assembly. The cover is then removed, the tissue culture medium is then removed from each chamber such as by aspiration or other techniques well known in the art.

Next the well frame 50 is easily separated and removed from the upper surface of the base member insert by lifting the well frame 50, causing the sealing means 70 to cleanly and easily separate from the upper surface of the base member insert. Because of the substantially reduced detachment forces needed to release the sealing means 70 from the upper surface 32 of the base insert 30 of the assembly taught herein, a separate tool such as a lever and the like, wedged between the well frame and the slide insert is not required, as typically practiced in the field.

Next, the mass of tissue and cells attached to the upper surface of the base insert can be rinsed and fixed on the base insert, wherein the affixed tissue and cell cultures can then be treated with appropriate stains to stain the cell or tissue cultures. Alternatively, prior to separating the well frame from the upper surface of the base member insert (i.e., while the wells are still assembled), the mass of tissue and cells attached to the upper surface of the base insert can be rinsed and fixed on the base insert, wherein the affixed tissue and cell cultures can then be treated with appropriate stains to stain the cell or tissue cultures.

The resulting base insert can then be microscopically examined and stored for further use. Additionally, the upper surface 32 of the base insert which the stained tissue and cells are adhered, can bear on the surface portion various identifying markings and permanent records of the results of the tissue and cell cultures grown.

Tissue and cell cultures produced, analyzed, transported and stored using the present invention is far simpler and more efficient when compared to the devices and techniques employed in the prior art.

Kits

The term “kit” includes, for example, each of the components combined in a single package, the components individually packaged and sold together, or the components presented together in a catalog (e.g., on the same page or double-page spread in the catalog).

In accordance with other aspects of the invention taught herein, the invention also provides for kits that include a cell culture assembly 20, 22, and 24 that may be used to grow cultures of cell and tissue test samples. The kit may comprise, for example, one or more cell culture assemblies. The kit may also contain one or more standard and/or customized microscope slide inserts 30. As an example, the kit may optionally include cells, reagents, media, and growth factors. The kits may also include slides with precoated ECM (extracellular matrix), precultured cells, antibodies, or detection molecules, just to name a few additional components.

The kit may also include a slide insert having one or more open through holes, wherein the through holes are in positional alignment with the well compartments in the well frame. In an alternative embodiment, one or more of the open through holes are covered by a porous matrix or membrane, such as the Biopore™ Membrane, from Millipore Corporation in Billerica, Mass., USA. The kit may also include instructions for using the cell culture assembly, as well as methods for growing cell and tissue cultures.

Therefore, it should be appreciated that the various embodiments of the invention provide advantages in simplifying and accelerating cell and tissue culture growth. Moreover, it has been found that the various embodiments also provide improved performance over conventional cell culture vessels, such as by minimizing cross-contamination between multiple tests samples with different well compartments on the upper surface of base member insert.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims are regarded as included within the subject matter of the inventions of the present disclosure.

What is claimed is:

1. A cell culture assembly system comprising:

a) a base member insert having an upper surface and a length; and b) a cell culture assembly having, i) a bottom support frame for receiving a first portion of said the base member insert less than said length, such that a second portion of said base member insert extends outwardly from said bottom support frame, said bottom support frame comprising a pair of opposite side walls and a cross member support connecting said opposite side walls, said opposite side walls defining between them a base member insert supporting surface that includes said cross member support, said base member insert being receivable between said pair of opposite side walls and being supportable by said supporting surface;

ii) a well compartment frame having sidewalls, each sidewall having an upper and lower surface, and one or more well compartments, each well compartment having an upper and a lower well compartment opening;

iii) a sealing element positioned on or within the lower surface of the well compartment frame adapted to operatively create a liquid-impermeable releasable seal between the upper surface of the first portion of the base member insert and the lower surface of the well compartment frame when the well frame is positioned on the upper surface of the first portion of the base member insert and the liquid-impermeable seal is compressed onto or otherwise sealingly engaged with the upper surface of the first portion of the base member insert, such that when the well compartment frame and base member insert are physically separated, the sealing element leaves the upper surface of the first portion of said base member insert free of sealing element material, iv) a fastening mechanism comprising a first element located on the support frame and a second element located on the well compartment frame, the first and second elements cooperatively engaging with one another for fastening the support frame to the well compartment frame when the assembly is in a closed position; and v) a removable cover adapted to be positioned over the upper well compartment opening, while also providing for air/gas exchange to maintain the pH of the culture medium and liquid reagents contained in each well compartment.

2. The assembly of claim 1, wherein the sealing element comprises an integral over-molded material selected from the group consisting of elastomers, thermoplastics, synthetic rubber, natural rubber or mixtures thereof.

3. The assembly of claim 1, wherein the sealing element comprises a material selected from the group consisting of elastomers, thermoplastics, synthetic rubber, natural rubber or mixtures thereof, and the sealing element is adhesively bonded to the lower surface of the well frame.

4. The assembly of claim 1, wherein the lower surface of the well compartment frame further comprises a groove for receiving the sealing element, and the sealing element comprises a material selected from the group consisting of elastomers, thermoplastics, synthetic rubber, natural rubber or mixtures thereof.

5. The assembly of claim 1, wherein the cover further comprises (1) a plurality of stacking ribs incorporated onto the top outer surface of the cover, thereby allowing multiple assemblies to be arranged in a stacked configuration one on top of the other, and (2) elongated ridges located on the underside of the cover thereby enclosing each well compartment opening to minimize contamination and evaporation in each well compartment.

6. The assembly of claim 1, further comprising a hinged attachment element for securing the support frame to the well compartment frame.

7. The assembly of claim 1, wherein the base member insert is a microscope slide.

8. The assembly of claim 1, wherein the base member insert is glass or plastic.

9. The assembly of claim 8, wherein the base member insert is plastic and further comprises:

a) one or more through holes covered with a membrane, wherein each through hole is sealed liquid tight along the hole perimeter, and each through hole is in positional alignment with a well compartment in the well compartment frame.

10. A cell culture assembly system comprising:

a) a base member insert having an upper surface and a length; and b) a one-piece cell culture assembly having, i) a bottom support frame for receiving a first portion of the base member insert less than said length, such that a second portion of said base member insert extends outwardly from said bottom support frame, said bottom support frame comprising a pair of opposite side walls and a cross member support connecting said opposite side walls, said opposite side walls defining between them a base member insert supporting surface that includes said cross member support, said base member insert being receivable between said pair of opposite side walls and being supportable by said supporting surface;

ii) a well compartment frame having sidewalls, each sidewall having an upper and lower surface, and one or more well compartments, each well compartment having an upper and a lower well compartment opening;

iii) a sealing element comprising an integral over-molded material selected from the group consisting of elastomers, thermoplastics, synthetic rubber, natural rubber or mixtures thereof, positioned on or within the lower surface of the well compartment frame adapted to operatively create a liquid-impermeable releasable seal between the upper surface of the first portion of the base member insert and the lower surface of the well compartment frame when the well compartment frame is positioned on the upper surface of the first portion of the base member insert and the liquid-impermeable seal is compressed onto or otherwise sealingly engaged with the upper surface of the first portion of the base member insert, such that when the well compartment frame and base member insert are physically separated, the sealing element leaves the upper surface of the first portion of the base member insert free of sealing element material, iv) a fastening mechanism comprising a first element located on the support frame and a second element located on the well compartment frame, the first and second elements cooperatively engaging with one another for fastening the support frame to the well compartment frame when the assembly is in a closed position; and v) a hinged attachment element for hingedly securing the support frame to the well compartment frame; and c) a removable cover having an underside, adapted to be positioned over the upper well compartment openings, and having elongated ridges located on the underside of the cover thereby enclosing each well compartment opening to minimize contamination and evaporation in each well compartment, while also providing for air/gas exchange to maintain the pH of the culture medium and liquid reagents contained in each well compartment.

11. A method for growing biological cultures using the assembly of claim 10 comprising the steps:

a) positioning the base member insert onto the support frame;

b) positioning the well compartment frame having the sealing element located on the lower surface onto the upper surface of the base member insert such that the sealing element creates a liquid-impermeable seal between the lower surface of the well compartment frame and the upper surface of the first portion of the base member insert, and thereby forming one or more well compartments on the upper surface of the first portion of the base member insert;

c) placing a biological culture medium into each individual well compartment onto the upper surface of the first portion of the base member insert;

d) introducing a biological test sample liquid into the biological culture medium positioned on the first portion of the base member insert;

e) placing the cover over the one or more well compartments on the upper surface of the first portion of the base member insert;

f) incubating the medium and the biological test sample under appropriate conditions to allow the sample to grow and to attach to the upper surface of the first portion of the base member insert;

g) removing the biological culture medium from each well compartment;

h) rinsing, fixing and staining the biological test sample directly in the well compartments;

i) separating the well compartment frame and the base member insert having the fixed and stained biological test sample attached onto the upper surface of the first portion of the base member insert; and j) microscopically examining the attached biological test sample.

12. The method of claim 11, wherein the biological test sample is a liquid.

13. The method of claim 11, wherein the biological test sample is selected from the group consisting of cells, tissues microorganisms and mixtures thereof.

14. A method for growing biological cultures using the assembly of claim 10 comprising the steps:

a) positioning the base member insert onto the support frame;

b) positioning the well compartment frame having the sealing element located on the lower surface onto the upper surface of the first portion of the base member insert such that the sealing element creates a liquid-impermeable seal between the lower surface of the well compartment frame and the upper surface of the base member insert, and thereby forming one or more well compartments on the upper surface of the first portion of the base member insert;

c) placing a biological culture medium into each individual well compartment onto the upper surface of the first portion of the base member insert;

d) introducing a biological test sample liquid into the biological culture medium positioned on the first portion of the base member insert;

e) placing the cover over the one or more well compartments on the upper surface of the first portion of the base member insert;

f) incubating the medium and the biological test sample under appropriate conditions to allow the biological test sample to grow and to attach to the upper surface of the first portion of the base member insert;

g) removing the biological culture medium from each well compartment;

h) separating the well compartment frame and the base member insert having the biological test sample attached onto the upper surface of the first portion of the base member insert;

h) rinsing, fixing and staining the biological test sample attached to the upper surface of the first portion of the base member insert; and j) microscopically examining the biological test sample attached to the upper surface of the first portion of the base member insert.

* * * * *